US00PP28804P3

(12) United States Plant Patent
Graff

(10) Patent No.: US PP28,804 P3
(45) Date of Patent: Dec. 26, 2017

(54) POINSETTIA PLANT NAMED 'QISMAS CRUNCH'

(50) Latin Name: ***Euphorbia pulcherrima* Willd.**
Varietal Denomination: Qismas Crunch

(71) Applicant: Poul Graff, Sabro (DK)

(72) Inventor: Poul Graff, Sabro (DK)

(73) Assignee: Graff Breeding A/S, Sabro (DK)

( * ) Notice: Subject to any disclaimer, the term of this patent is extended or adjusted under 35 U.S.C. 154(b) by 161 days.

(21) Appl. No.: 14/756,184

(22) Filed: Aug. 12, 2015

(65) Prior Publication Data

US 2017/0049024 P1 Feb. 16, 2017

(51) Int. Cl.
*A01H 5/02* (2006.01)

(52) U.S. Cl.
USPC ..... Plt./307

(58) Field of Classification Search
USPC ..... Plt./263.1, 302, 303, 307
See application file for complete search history.

(56) References Cited

PUBLICATIONS

PLUTO: Plant Variety Database, Mar. 9, 2017, citation for 'Qismas Crunch'. 1 page.*

* cited by examiner

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of Poinsettia plant named 'Qismas Crunch', characterized by its compact, upright and uniformly mounding plant habit; moderately vigorous growth habit; freely branching habit; dark green-colored leaves that are twisting and "curly" in appearance; large and full inflorescences with numerous dark red-colored flower bracts; and excellent post-production longevity.

2 Drawing Sheets

Botanical designation: *Euphorbia pulcherrima* Willd.
Cultivar denomination: 'QISMAS CRUNCH'.

BACKGROUND OF THE INVENTION

The present invention relates to a new and distinct cultivar of Poinsettia plant, botanically known as *Euphorbia pulcherrima* Willd. and hereinafter referred to by the name 'Qismas Crunch'.

The new Poinsettia plant is a product of a planned breeding program conducted by the Inventor in Sabro, Denmark. The objective of the breeding program is to create uniform and freely-branching Poinsettia plants with attractive inflorescences and good postproduction longevity.

The new Poinsettia plant is a naturally-occurring whole plant mutation of *Euphorbia pulcherrima* Willd. 'Eckalverta', disclosed in U.S. Plant Pat. No. 13,297. The new Poinsettia plant was discovered and selected by the Inventor as a single flowering plant within a population of plants of 'Eckalverta' in a controlled greenhouse environment in Sabro, Denmark in May, 2011.

Asexual reproduction of the new Poinsettia plant by terminal vegetative cuttings in a controlled greenhouse environment in Sabro, Denmark since September, 2011 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Qismas Crunch'. These characteristics in combination distinguish 'Qismas Crunch' as a new and distinct Poinsettia plant:

1. Compact, upright and uniformly mounding plant habit.
2. Moderately vigorous growth habit.
3. Freely branching habit.
4. Dark green-colored leaves that are twisting and "curly" in appearance.
5. Large and full inflorescences with numerous dark red-colored flower bracts.
6. Excellent post-production longevity.

Plants of the new Poinsettia can be compared to plants of the parent, 'Eckalverta'. Plants of the new Poinsettia differ primarily from plants of 'Eckalverta' in the following characteristics:

1. Plants of the new Poinsettia are more compact than plants of 'Eckalverta'.
2. Leaves of plants of the new Poinsettia are "curly" whereas leaves of plants of 'Eckalverta' are flat.
3. Flower bracts of plants of the new Poinsettia are more horizontal and twisting than and not as upright and flat as flower bracts of plants of 'Eckalverta'.
4. Plants of the new Poinsettia have shorter peduncles than plants of 'Eckalverta'.

Plants of the new Poinsettia can be compared to plants of *Euphorbia pulcherrima* Willd. 'Happy Day', not patented. In side-by-side comparisons conducted in Sabro, Denmark, plants of the new Poinsettia differed primarily from plants of 'Happy Day' in the following characteristics:

1. Flower bracts of plants of the new Poinsettia were more twisting than and not as flat as flower bracts of plants of 'Happy Day'.
2. Flower bracts of plants of the new Poinsettia had entire margins with pointed lobes whereas flower bracts of plants of 'Happy Day' had entire margins without lobes.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet is a side perspective view of a typical flowering plant of 'Qismas Crunch' grown in a container.

The photograph on the second sheet is a close-up view of a typical dissected inflorescence of 'Qismas Crunch'.

DETAILED BOTANICAL DESCRIPTION

The aforementioned photographs and following observations, measurements and values describe plants grown during the winter in 13-cm containers in a glass-covered greenhouse in Sabro, Denmark and under cultural practices typical of commercial Poinsettia production. During the production of the plants, day temperatures ranged from 20° C. to 25° C., night temperatures ranged from 19° C. to 21° C. and light levels ranged from 40 to 50 klux. Plants were pinched one time eight weeks after planting and plants were 20 weeks old when the photographs and the description were taken. In the description, color references are made to The Royal Horticultural Society Colour Chart, 2001 Edition, except where general terms of ordinary dictionary significance are used.

Botanical classification: *Euphorbia pulcherrima* Willd. 'Qismas Crunch'.

Parentage: Naturally-occurring whole plant mutation of *Euphorbia pulcherrima* Willd. 'Eckalverta', disclosed in U.S. Plant Pat. No. 13,297.

Propagation:

*Type.*—Terminal vegetative cuttings.

*Time to initiate roots, summer.*—About three weeks at temperatures about 24° C.

*Time to initiate roots, winter.*—About four weeks at temperatures about 24° C.

*Time to produce a rooted young plant, summer.*—About eight weeks at temperatures about 24° C.

*Time to produce a rooted young plant, winter.*—About ten weeks at temperatures about 24° C.

*Root description.*—Medium in thickness, fleshy; color, close to 158A, actual color of the roots is dependent on substrate composition, water quality, fertilizer type and formulation, substrate temperature and physiological age of roots.

*Rooting habit.*—Freely branching; dense.

Plant description:

*Plant and growth habit.*—Compact, upright and uniformly mounded plant habit; inverted triangle with rounded crown; large full inflorescences positioned above the foliar plane; moderately vigorous growth habit and moderate growth rate.

*Plant height.*—About 20 cm to 40 cm.

*Plant diameter or spread.*—About 30 cm to 50 cm.

*Lateral branch description.*—Branching habit: Freely branching habit, about three to six lateral branches develop after pinching. Length: About 15 cm to 25 cm. Diameter: About 3 mm to 6 mm. Internode length: About 1 cm to 5 cm. Strength: Strong. Texture: Smooth, glabrous. Angle: Mostly upright. Color: Close to 189A.

*Leaf description.*—Arrangement and appearance: Alternate, simple. Length: About 8 cm to 12 cm. Width: About 7 cm to 10 cm. Shape: Broadly ovate. Apex: Acute. Base: Obtuse. Margin: Entire, shallowly lobed. Venation pattern: Pinnate. Aspect: Twisting, "curly" appearance. Texture, upper and lower surfaces: Smooth, glabrous; leathery. Color: Developing leaves, upper surface: Close to 137A. Developing leaves, lower surface: Close to 138A. Fully expanded leaves, upper surface: Close to N189A; venation, close to N200C. Fully expanded leaves, lower surface: Close to 189A, venation, close to N200D. Petioles: Length: About 0.5 cm to 2 cm. Diameter: About 2 mm to 6 mm. Texture, upper and lower surfaces: Smooth, glabrous. Color, upper surface: Close to 166A. Color, lower surface: Close to 174A.

Inflorescence description:

*Inflorescence type and habit.*—Large full inflorescences are compound corymbs of cyathia with dark red-colored flower bracts subtending the cyathia; one inflorescence per lateral branch with inflorescences positioned above and beyond the foliar plane.

*Fragrance.*—None detected.

*Natural flowering season.*—Plants flower naturally during the winter under long nyctoperiod conditions; inflorescence initiation and development can be induced under artificial long nyctoperiod conditions; mid-season flowering habit, response time is about nine to ten weeks after start of long nyctoperiod conditions.

*Post-production longevity.*—Excellent post-production longevity; plants of the new Poinsettia maintain good substance and bract color for about four to six weeks under interior conditions; flower bracts persistent.

*Inflorescence diameter.*—About 15 cm to 20 cm.

*Inflorescence height.*—About 8 cm to 12 cm.

*Flower bracts.*—Quantity per inflorescence: About 20 to 25. Length: About 8 cm to 10 cm. Width: About 4 cm to 7 cm. Shape: Obovate. Apex: Cuspidate. Base: Obtuse. Margin: Entire, lobed. Venation: Pinnate. Texture, upper surface: Rough, glabrous; velvety. Texture, lower surface: Rough, glabrous; satiny. Aspect: Twisting. Color: Developing and fully expanded bracts, upper surface: Close to 45B; color becoming closer to 60A with development. Developing and fully expanded bracts, lower surface: Close to 46C; color becoming closer to 185B with development. Bract petioles: Length: About 5 mm to 10 mm. Diameter: About 2 mm. Texture, upper and lower surfaces: Smooth, glabrous. Color, upper surface: Close to 46A. Color, lower surface: Close to 143A.

*Cyathia.*—Quantity per corymb: About 15 to 20. Length: About 5 mm to 15 mm. Width: About 5 mm. Shape: Oval. Color, developing, inner surface: Close to 154C. Color, developing, outer surface: Close to 138A. Color, fully developed, inner surface: Close to 144D. Color, fully developed, outer surface: Close to 143A. Nectaries: Quantity per cyathium: Typically one. Length: About 3 mm. Diameter: About 5 mm. Shape: Fan-shaped. Texture, inner and outer surfaces: Smooth, glabrous. Color, developing, inner surface: Close to 144C. Color, developing, outer surface: Close to 144B. Color, fully developed, inner surface: Close to 144D. Color, fully developed, outer surface: Close to 2A.

*Peduncles.*—Length: About 5 mm to 15 mm. Diameter: About 3 mm to 5 mm. Strength: Strong. Texture: Smooth, glabrous. Angle: Mostly upright. Color: Close to 144A.

*Reproductive organs.*—Stamens: Quantity per cyathium: About 10 to 30. Filament length: About 1 mm to 5 mm. Filament color: Close to 60B. Anther shape: Round. Anther length: About 1 mm. Anther color: Close to 164B. Amount of pollen: Moderate. Pollen color: Close to 164C. Pistils: Quantity per cyathium: Typically one. Pistil length: About 1 mm to 2 mm. Style length: About 1 mm to 2 mm. Style color: Close to 145A. Stigma shape: Four-parted. Stigma color: Close to 59A. Ovary color: Close to 143A. Seeds and fruits: Seed and fruit production has not been observed on plants of the new Poinsettia to date.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from 12° C. to 37° C.

It is claimed:

1. A new and distinct Poinsettia plant named 'Qismas Crunch' as illustrated and described.

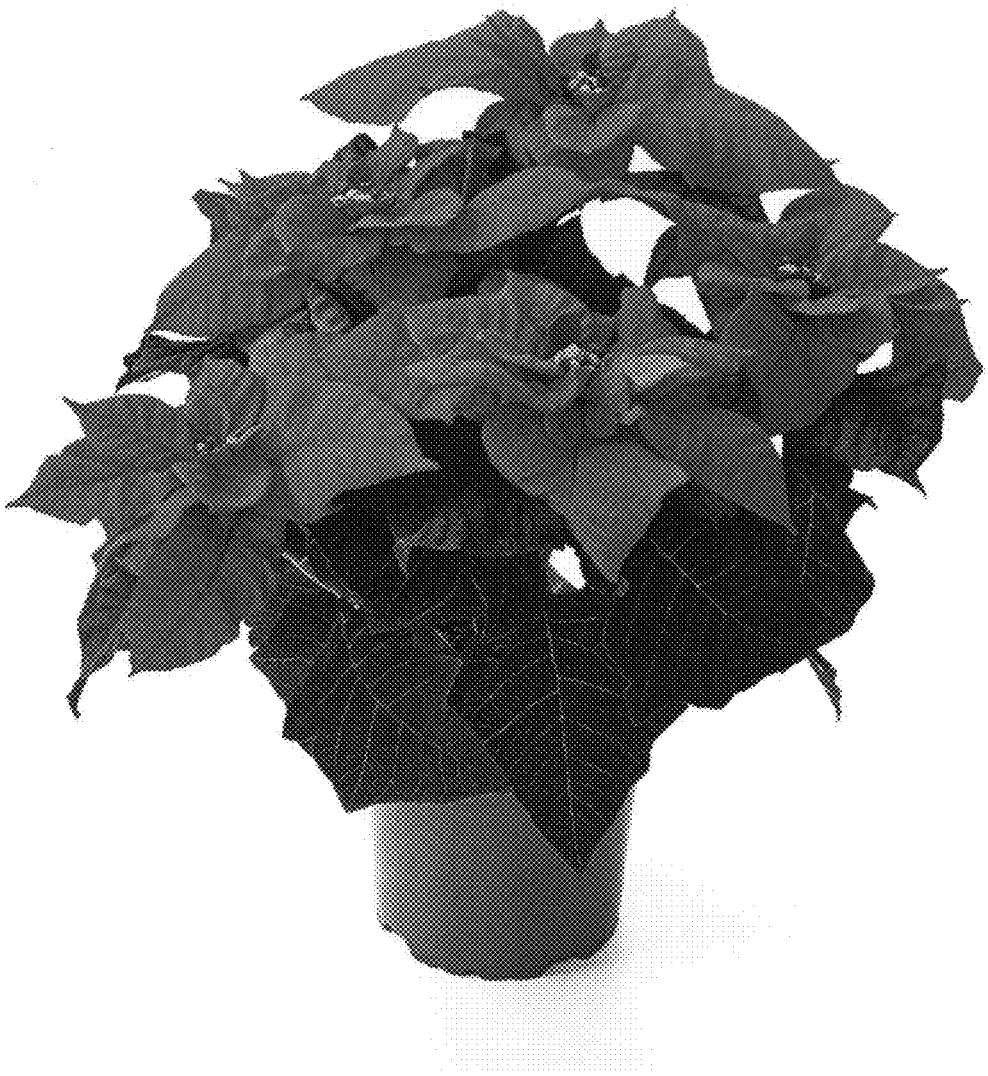

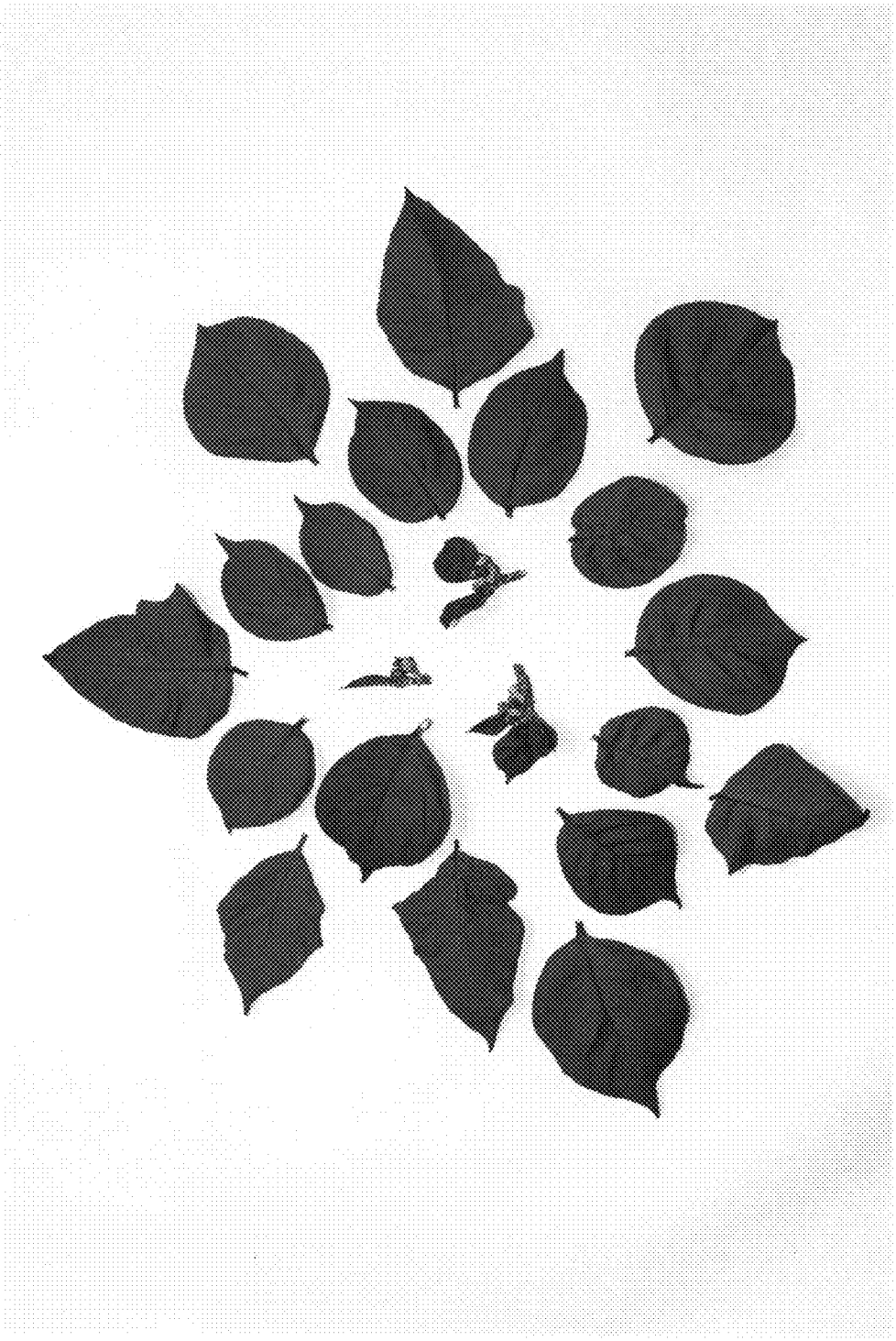

* * * * *